United States Patent [19]

Rajadhyaksha

[11] Patent Number: 5,482,965
[45] Date of Patent: Jan. 9, 1996

[54] COMPOSITIONS AND METHOD COMPRISING AMINOALCOHOL DERIVATIVES AS MEMBRANE PENETRATION ENHANCERS FOR PHYSIOLOGICAL ACTIVE AGENTS

[76] Inventor: Vithal J. Rajadhyaksha, 27436 Esqina, Mission Viejo, Calif. 92691

[21] Appl. No.: 115,772

[22] Filed: Sep. 3, 1993

Related U.S. Application Data

[63] Continuation of Ser. No. 672,020, Mar. 19, 1991, abandoned.

[51] Int. Cl.$^6$ .................. A61K 31/27; A61K 31/335; A61K 31/22; A61K 31/225; A61K 31/23; A61K 31/16
[52] U.S. Cl. .................. 514/452; 514/478; 514/479; 514/546; 514/547; 514/552; 514/625; 514/629; 514/946; 514/947
[58] Field of Search .................. 514/847, 785, 514/478, 479, 452, 546, 547, 552, 625, 629, 946, 947

[56] References Cited

U.S. PATENT DOCUMENTS

| | | | |
|---|---|---|---|
| 2,247,256 | 6/1941 | Senkus | 260/338 |
| 2,260,265 | 10/1941 | Senkus | 260/338 |
| 2,317,555 | 4/1943 | Robinette | 252/357 |
| 2,320,707 | 6/1943 | Robinette | 252/355 |
| 2,346,454 | 4/1944 | Robinette | 252/8.75 |
| 2,370,586 | 2/1945 | Senkus | 260/338 |
| 2,383,622 | 8/1945 | Senkus | 260/338 |
| 2,399,068 | 4/1946 | Senkus | 260/338 |
| 2,415,021 | 1/1947 | Morey | 260/338 |
| 2,485,987 | 10/1949 | Senkus | 167/33 |
| 2,527,078 | 10/1950 | Tucker | 252/117 |
| 4,950,688 | 8/1990 | Bowsert et al. | 514/847 |
| 5,149,860 | 9/1992 | Zysman et al. | 560/160 |
| 5,198,470 | 3/1993 | Zysman et al. | 514/785 |

FOREIGN PATENT DOCUMENTS

| | | |
|---|---|---|
| 2652002 | 3/1991 | France . |
| 0268460 | 11/1987 | WIPO . |
| WO88/04938 | 7/1988 | WIPO . |

*Primary Examiner*—T. J. Criares
*Attorney, Agent, or Firm*—Knobbe, Martens, Olson & Bear

[57] ABSTRACT

A method and compositions for enhancing absorption of topically administered physiologically active agents through the skin and mucous membranes of humans and animals in a transdermal device or formulation for local or systemic use, comprising a therapeutically effective amount of a pharmaceutically active agent and a non-toxic, effective amount of penetration enhancing agent of the formula I or a physiologically acceptable salt thereof:

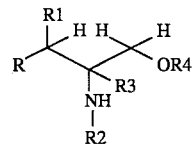

wherein:

$R^1$, $R^2$, $R^3$ and $R^4$ are as defined herein.

26 Claims, No Drawings

COMPOSITIONS AND METHOD COMPRISING AMINOALCOHOL DERIVATIVES AS MEMBRANE PENETRATION ENHANCERS FOR PHYSIOLOGICAL ACTIVE AGENTS

This is a continuation of application Ser. No. 07/672,020, filed Mar. 19, 1991, now abandoned.

FIELD OF THE INVENTION

This invention relates to aminoalcohols and their derivatives as penetration-enhancers for pharmaceutical, agricultural and cosmetic agents.

BACKGROUND OF THE INVENTION

Many physiologically active agents are best applied topically to obtain desirable results. Topical application, in the form of creams, lotions, gels, solutions, etc., largely avoids side effects of the agents and permits high level concentrations of the agents.

Some therapeutic drugs may also be administered for systemic use through the skin or other body membranes including intranasal and intravaginal application of humans and other animals, utilizing a transdermal device or formulated in a suppository or aerosol spray. For some years, pharmaceutical researchers have sought an effective means of introducing drugs into the bloodstream by applying them to the unbroken skin. Among other advantages, such administration can provide a comfortable, convenient and safe way of giving many drugs now taken orally or infused into veins or injected intramuscularly.

Using skin as the portal for drug entry offers unique potential, because transdermal delivery permits close control over drug absorption. For example, it avoids factors that can cause unpredictable absorption from gastrointestinal tract, including changes in acidity, motility, and food content. It also avoids initial metabolism of the drug by the liver known as the first pass effect. Thus, controlled drug entry through skin can achieve a high degree of control over blood concentrations of drug.

Close control over drug concentration in blood can translate readily into safer and more comfortable treatment. When a drug's adverse effects occur at higher concentrations than its beneficial ones, rate control can maintain the concentration that evoke only—or principally the drug's desired actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal system that require application infrequently—in some cases, only once or twice weekly and reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, those susceptible to a higher first pass liver metabolism or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of drug to the circulation over prolonged periods of time to obtain a uniform delivery rate and blood level of drug. Commencement and termination of drug therapy are initiated by the application and removal of the dosing devices from the skin. Uncertainties of administration through the gastrointestinal tract and the inconvenience of administration by injection are eliminated. Since a high concentration of drug never enters the body, problems of pulse entry are overcome and metabolic half-life is not a factor of controlling importance.

The greatest problems in applying physiologically active agents topically or transdermally is that the skin is an effective barrier to penetration. The epidermis of the skin has an exterior layer of dead cells called the stratum corneum which is tightly compacted and oily and which provides an effective barrier against gaseous, solid or liquid chemical agents, whether used alone or in water or in oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use of treating such conditions as inflammation, acne, psoriasis, herpes labialis, herpes genitalis, eczema, infections caused by fungi, viruses and other microorganisms, or or, her disorders or conditions of the skin or mucous membranes or of conditions beneath the exterior surface of the skin or mucous membranes. The stratum corneum also prevents the skin from absorbing and retaining cosmetic-type materials such as sunscreens, perfumes, mosquito repellents and the like.

Physiologically active agents may be applied to the locally affected parts of the body in the form of a solution, cream, lotion or gel utilizing the vehicle system described herein. These agents may also be delivered for systemic use utilizing the vehicle system in a transdermal patch. Vehicles such as USP cold cream, ethanol and various ointments, oils, solvents and emulsions have been used heretofore to apply physiologically active ingredients locally. Most such vehicles are not effective to carry significant amounts of physiologically active agents into and through the skin. One such vehicle is dimethyl sulfoxide, which is described in U.S. Pat. No. 3,551,554.

My previous inventions disclosed in U.S. Patent Nos. 3,989,816; 3,991,203; 4,122,170; 4,316,893; 4,405,616; 4,415,563; 4,423,040; 4,424,210; 4,444,762; 4,837,026 and 4,876,249 describe a method for enhancing the topical or transdermal administration of physiologically active agents by combining such an agent with an effective amount of a penetration enhancer and applying the combination to skin or other body membranes of humans or animals, in the form of solution, cream, gel, lotion, or a transdermal device.

My related U.S. Patent Nos. 4,461,638 and 4,762,549 describe a method for enhancing delivery of plant nutrients and plant growth regulators, and my U.S. Pat. No. 4,525,199 describes an improved method of pest control by enhancing pesticide permeation.

My related U.S. application, Ser. No. 218,316, filed on Jul. 12, 1988, describes a method for enhancing topical and transdermal administration of physiologically active agents with membrane penetration enhancers selected from oxazolidone and related heterocyclic compounds.

My related U.S. application Set. No. 07/348,387, filed on May 8, 1989 describes a method for enhancing topical and transdermal administration of physiologically active agents with yet another series of membrane penetration enhancers.

My related U.S. applications Ser. No. 07/393,584, filed on Aug. 11, 1989 and Set. No. 07/451,124, filed on Dec. 15, 1989, C.I.P.s of U.S. patent application Ser. No. 002,387, filed on Jan. 12, 1987, now U.S. Pat. No. 4,876,249, describe a method for enhancing topical and transdermal administration of physiologically active agents with membrane penetration enhancers selected from heterocyclic compounds containing two heteroatoms.

Penetration enhancers for enhancing systemic administration of therapeutic agents transdermally disclosed in the art include dodecyl pyrrolidone, dimethyl lauramide, dimethyl sulfoxide, decyl methyl sulfoxide, ethanol, 1-dodecyl-hexahydro-2H-azepin-2-one, 1-dodecanoyl hexamethylenimine, 2-nonyl-1,3-dioxolane, fatty acids and their esters, sucrose esters etc. These agents may be used prior to or concurrently with administration of the active agent, see, e.g., U.S. Pat. Nos. 4,031,894; 3,996,934 and 3,921,636.

SUMMARY OF THE INVENTION

One of the main function of the epidermis is the production of a cohesive, relatively impermeable outer sheath. It has been known that from the time an epidermal cell leaves the basal layer to the time it is desquamated, the cell lipids change both qualitatively and quantitatively. A phospholipid is the most abundant lipid class in basal cell, whereas half of the lipid in a desquamated cell consists of ceramide. The lipid content of desquamated stratum corneum cell is approximately six time that of basal cell. The change in lipid composition of a cell undergoing cornification results mainly from de nuvo synthesis of cholesterol, fatty acid and ceramide.

This invention relates to penetranion enhancers closely related to the constituents of the epidermal outer sheath and therefore interact with it without irreversible disruption of the barrier. Moreover, these enhancers possess an advantage that they are expected to yield nontoxic, pharmacologically inert metabolites after passage through the skin and the systemic circulation. The invention further relates to compositions for carrying physiologically active agents through body membranes such as skin and mucosa for retaining these agents in the body tissues and further relates to a method of administering systemically and locally active agents through the skin or other body membranes of humans and animals, utilizing a transdermal device or formulation, containing an effective, non-toxic amount of a membranae penetration enhancer having the structural formula I:

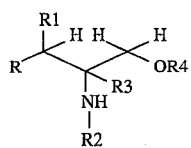

wherein:

R is selected from H, and an aliphatic hydrocarbon group with from about i to about 20 carbon atoms, optionally containing a heteroatom in the hydrocarbon chain;

R1 is selected from H, OH or O-CO-RS, where R5 is an aliphatic hydrocarbon group with from about 1 to about 18 carbon atoms;

R2 is selected from H, a lower aliphatic hydrocarbon group, acyl, hydroxyacyl or alkoyloxyacyl group with up to about 40 carbon atoms;

R3 is selected from H, an aliphatic hydrocarbon group, with up to about 16 carbon atoms unsubstituted or substituted with hydroxy, acyloxy or alkylthio or an aryl or aralkyl group; and R4 is H or an acyl group with from about 1 to about 18 carbon atoms; or when R1 is OH, R1 and R4 are combined to form compounds having a 1,3 -dioxane ring,

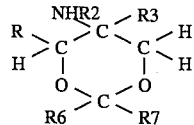

wherein, R6 and R7 are selected from H, an aliphatic hydrocarbon group unsubstituted or substituted with hydroxy, acyloxy, or carboalkoxy, or an aryl group, or they may combine to form a carbonyl group, or a physiologically acceptable salt thereof.

It is understood that the aliphatic hydrocarbon groups in the substituents R–R7 may be straight or branched and saturated or unsaturated, such as straight or branched chained alkyl, alkenyl or alkinyl groups. In the substituents where the hydrocarbon group may contain a heteroatom (R), this heteroatom usually is S or O.

It will be readily appreciated by those skilled in the art that certain compounds represented by formula I may exhibit optical and geometric isomerism. However, where no designation of isomers is specified with respect to the compounds of this invention, it is to be understood that all possible stereoisomers and geometric isomers (E and Z), and racemic and optically active compounds are included.

It will also be readily appreciated by those skilled in the art that certain of the compounds described in the disclosure may form salts with carboxylic and mineral acids and it is understood that all such salts, in particular the physiologically acceptable salts, are included in the invention.

In one preferred embodiment of I, R is an alkyl group with from 1 to 20 carbon atoms, R1 and R3 are H, R2 is an acyl group with from 1 to 30 carbon atoms and R4 is an acyl group with from 1 to 18 carbon atoms.

In another preferred embodiment of I, R1 is -O-CO-R5, wherein R5 is an alkyl group with from 1 to 18 carbon atoms and R, R2, R3 and R4 are as defined above.

Yet in another preferred embodiment of I, R1 is OH, R2 is H or acyl, R3 and R4 are H and R1 and R4 are combined to form a 1,3-dioxane ring and R, R6 and R7 are as defined above.

Yet in another preferred embodiment of I, R1 is OH, R2 is H or acyl, R3 is alkyl, aryl, aralkyl, hydroxyalkyl, acyloxyalkyl or alkylthioalkyl, R and R4 are H and R1 and R4 are combined to form a 1,3-dioxane ring, wherein R6 and R7 are as defined above.

It has been found that the physiologically active agents are carried through body membranes by the claimed penetration enhancers and are retained in the body tissue when applied topically in form of a cream, gel, or lotion or absorbed systemically when applied in the form of a transdermal device or formulation, for example, as a transdermal patch, a rectal or vagina suppository, as a nasal spray or when incorporated in a vaginal sponge or tampon.

This invention also relates to the problems such as skin irritation and skin sensitization that are commonly associated with conventional penetration enhancers found in the prior art. Since the compounds of this invention are structurally closely related to the ceramides, the lipids primarily present in the top layers of the skin, it is believed that skin irritation and skin sensitization can be avoided significantly with the use of these compounds as enhancers in the therapeutic compositions.

The invention further relates the penetration enhancers themselves and their method of making.

DETAILED DESCRIPTION OF THE INVENTION

Typical examples of compounds included in the foregoing formula I of this invention are the following:

1) 2-Ethanoylaminododecyl ethanoate
2) 2-Octanoylaminododecyl octanoate
3) 2-Octadec-9-enoylaminododecyl octadec-9-enoate
4) 2-Octadec-9-enoylaminododecyl ethanoate
5) 2-Octadecanoylaminooctadec-4-enyl-1,3-diethanoate
6) 2-Ethanoylaminooctadec-4-enyl 1,3-diethanoate
7) 2-Ethanoylaminooctadecyl 1,3-diethanoate
8) 5-Amino-2,2-dimethyl-4-(pentadec-1-enyl)-1,3-dioxane
9) 5-Amino-2,2-dimethyl-4-pentadecyl-1,3-dioxane
10) 5-Amino-4-(pentadec-1-enyl)-1,3-dioxan-2-one
11) 5-amino-4-dodecyl-1,3-dioxan-2-one
12) 4-Dodecyl-5-ethanoylamino-1,3-dioxan-2-one
13) 2-Ethanoylaminododecyl octadec-9-enoate
14) 2-Ethanoylamino-3-octadecyloxypropyl ethanoate
15) 5-Amino-2,2-dimethyl-4-(2,6,10,14-tetramethylpentadecyl)-1,3-dioxane
16) 5-Amino-2,2-dimethyl-4-(2,6-dimethyl-5-heptenyl)-1,3-dioxane
17) 5-amino-5-ethyl-2-undecyl-1,3-dioxane
18) 5-amino-2,2-dimethyl-5-undecyl-1,3-dioxane
19) 2,2-Dimethyl-5-dodecanoylamino-5-ethyl-1,3-dioxane
20) 5-Amino-5-ethyl-2-(3-heptyl)-1,3-dioxane
21) 5-Amino-5-hydroxymethyl-2-(3-heptyl)-1,3-dioxane
22) 5-Amino-5-ethyl-2-carbobutoxyethyl-2-methyl-1,3-dioxane
23) 5-Dodecanoylamino-5-methyl-1,3-dioxan-2-one
24) 5-Amino-5-undecyl-1,3-dioxan-2-one.

The following compounds, encompassed by general formula I of this invention are known in the literature.

The 4E,2S,3R isomer of compound 6 is the triacetyl derivative of naturally occurring D-erythro-Sphingosine and has been synthesized by Findeis and Whitesides, J. Org. Chem. 52, 2838 (1987); Julina et. al. Helv. Chim. Acta 69, 368 (1986) and references cited therein; Schmidt and Zimmermann, Tet. Lett. 27, 481 (1986). The 2-octadecanoylamino 2S,3R 1,3-diol derivative of compound 5, a ceramide, has been synthesized by Julina et. al., loc. cit. Compound 7 is the dihydro derivative of compound 6 and the 2S,3R isomer has been prepared by Roush and Adam, J. Org. Chem. 50, 3752 (1985). The E isomer of the 4R,5S stereoisomers of compounds 8 and its corresponding 1-heptadecenyl analog have been synthesized, Hasegawa and Kiso, JPN. Kokai Tokyo Koho JP 62,207,247 [87,207,247], 11 Sep 1987, C.A., 108:P167212 (1988), Hino et. al. J. Chem. Soc. Perkin Trans. I, 1687 (1986) and both E and Z isomers have been prepared by Kiso et. al., Carbohydr. Res. 158, 101 (1986) and J. Carbohydr. Chem. 5, 335 (1986). 4R,5S isomer of Compound 9 have been prepared by Nakagawa et. al., Tet. Lett. 6281 (1987) during the synthesis of Cerebroside B1$_b$. and Saitoh et. al. Bull. Chem. Soc. Japan, 54, 488 (1981), who also prepared the 4-[(Z)-3pentadecenyl] analog of Compound 8 during the total synthesis of two prosopis alkaloids. Compounds 15 and 16 have been prepared by Umemura and Mori, Agric. Biol. Chem., 46, 1797 (1982) as intermediates in the synthesis of spinghosine analogs. Compound 17 and related 5-amino-1,3-dioxanes have been prepared by Senkus, J. Amer. Chem. Soc. 63, 2635 (1941), ibid., 65, 1656 (1943) and U.S. Pat. Nos. 2,247,256, 2,260,265, 2,370,586, 2,383,622, 2,399,068 and evaluated as coating compounds, as intermediates for the preparation of insecticides and surface active agents and as insecticides, U.S. Pat. No. 2,485,987 and by CIBA Ltd., Fr.1,457,767, as intermediates in the preparation of isonitriles useful as insecticides, acaricides, ovicides, herbicides, fungicides, bactericides, and molluscicides. Robinette, U.S. Pat. Nos. 2,317,555, 2,320,707 and 2,346,454, has studied the 5-amino-1,3-dioxanes as wetting, penetrating & cleansing agents for various textile and leather treatments. The 2-unsubstituted analog of Compound 19 has been utilized by Tucker, U.S. Patent No. 2,527,078, as an ingredient in detergent mixture for inhibiting the precipitation of lime soaps. Compound 20, 21 and analogs have been prepared and investigated by Senkus for insecticidal properties. Compound 22 has been prepared by Morey, U.S. Pat. No. 2,415,021. Aliphatic substituted 1,3-dioxacycloalkanes, without the prerequisite amino or substituted amino functionality of this invention, have been disclosed as skin penetration enhancers by Samour and Daskalakis, Eur. Pat. Appl. EP 268,460, 25 May 1988 and particularly, 2-nonyl-1,3-dioxolane, Proceed. Intern. Symp. Control Rel. Bioact. Mater. 17, 415 (1990) and references cited therein.

To my knowledge the other compounds are novel.

The use of the compounds of the present invention as penetration enhancers in drug delivery is, however, novel and not predictable from the prior art.

The aminoalcohol derivatives covered by the general formula I may be prepared by any of the processes known in the literature, and are hereby incorporated by reference. For example, Ohashi et. al., Tet. Lett. 29, 1185 (1988); Findeis and Whitesides, J. Org. Chem. 52, 2838 (1987); Nakagawa et. al., Tet. Lett. 6281 (1987); Hino et. al., J. Chem. Soc. Perkin Trans. I, 1687 (1986); Koike et. al., Carbohydr. res. 158, 113 (1986), Kiso et. al., Carbohydr. Res. 158, 101 (1986) and J. Carbohydr. Chem. 5, 335 (1986); Schmidt and Zimmermann, Tet. Lett. 481 (1986); Julina et. al. Helv. Chim. Acta 69, 368 (1986); Roush and Adam, J. Org. Chem. 50, 3752 (1985); Bernet and Vasella, Tet. Lett. 24, 5491 (1983); Chandrakumar and Hajdu, J. Org.

Chem. 48, 1197 (1983); Garigipati and Weinreb, J. Amer. Chem. Soc. 105, 4499 (1983); Schmidt and Klaeger, Angew. Chem. Suppl. 393 (1982) and Angew. Chem. Int. Ed. 21, 982 (1982); Umemura and Mori, Agric. Biol. Chem. 46, 1797 (1982); Saitoh et. al., Bull. Chem. Soc. Japan 54, 488 (1981); Newman, J. Amer. Chem. Soc. 95, 4098 (1973) and Shapiro et. al., J. Amer. Chem. Soc. 80, 1194 (1958). In addition, the acetal and ketal derivatives of 5-amino-1,3-dioxane can be prepared from the nitro alcohols according to the methods of Senkus mentioned earlier and the corresponding 2-oxo derivatives by processes known for carbonyl group insertion, such as those outlined in my pending U.S. application Ser. No. 218,316, filed on Jul. 12, 1988, followed by hydrogenation of the nitro group. 5-Acylamino-1,3-dioxanes can be easily prepared by acylation of the 5=amino compounds with an appropriate carboxylic acid derivative according to the well established methods in the literature. 5-Amino-1,3-dioxanes with other substituents in 2-position can be prepared by the treatment of the said nitro alcohols with compounds containing a carbonyl group and the desired functionality, for example, with butyl levulinate as outlined by Morey. Other amino alcohols can be prepared as outlined in my pending U.S. application Ser. No. 218,316, filed on Jul. 12, 1988 and derivatized to compounds of formula I.

The compounds of the present invention may be used as penetration enhancers in the same manner as described in my U.S. Pat. Nos. 3,989,816; 3,991,203; 4,415,563; 4,122,170; 4,316,893; 4,405,616; 4,415,563; 4,423,040; 4,424,210; 4,444,762; 4,837,026 4,876,249 and U.S. applications Ser. No. 218,316, filed on Jul. 12, 1988; Ser. No. 07/348,387 filed May 8, 1989; Ser. No. 07/393,584, filed Aug. 11, 1989, and Ser. No. 07/451,124, filed on Dec. 15, 1989, which are hereby incorporated by reference.

The compounds of the present invention are useful as penetration enhancers for a wide range of physiologically active agents and the compositions disclosed herein are useful for topical and transdermal therapeutic application of these agents. Typically systemically active agents which may be delivered transdermally are therapeutic agents which are sufficiently potent such that they can be delivered through the skin or other membranes to the bloodstream in sufficient quantities to produce the desired therapeutic effect. In general this includes agents in all of the major therapeutic areas including, but not limited to, anti-infectives, such as antibiotics and antiviral agents, analgesics and analgesics combinations, anorexics, anthelmintics, antiarthritics, antiasthma agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarryhthmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, sedatives, tranquilizers and antiosteoporos is agents.

The subject compositions are also useful for topical application of many physiologically active agents in combination with the compounds of this invention.

Fungistatic and fungicidal agents such as, for example, thiabendazole, chloroxine, amphotericin, candicidin, fungimycin, nystatin, chlordantoin, clotrimazole, miconazole and related imidazole antifungal agents, pyrrolnitrin, salicylic acid, fezatione, ticlatone, tolnaftate, triacetin and zinc and sodium pyrithione may be combined with the compounds described herein and topically applied to affected areas of the skin. For example, fungistatic or fungicidal agents so applied are carried through the stratum corneum, and thereby successfully treat fungus-caused skin problems. These agents, thus applied, not only penetrate more quickly, but additionally enter the animal tissue in high concentrations and are retained for substantially longer time periods whereby a far more successful treatment is effected.

For example, the subject composition may also be employed in the treatment of fungus infections on the skin caused by candida and dermatophytes which cause athletes foot or ringworm, by incorporating thiabendazole or similar antifungal agents with one of the enhancers and applying it to the affected area.

The subject compositions are also useful in treating skin problems, such as for example, those associated with the herpes viruses, which may be treated with a cream of iododeoxyuridine or acyclovir in combination with one of the enhancers, or such problems as warts which may be treated with agents such as podophylline combined with one of the enhancers. Skin problems such as psoriasis may be treated by topical application of a conventional topical steroid formulated with one of the enhancers or by treatment with methotrexate incorporated with one of the enhancers of this invention. Scalp conditions such as alopecia arcata may be treated more effectively by applying agents such as minoxidil in combination with one of the enhancers of this invention directly to the scalp.

The subject compositions are also useful for treating mild eczema, for example, by applying a formulation of Fluocinolone acetonide or its derivatives; hydrocortisone or triamcinolone acetonide incorporated with one of the enhancers to the affected area.

Examples of other physiologically active steroids which may be used with the enhancers include corticosteroids such as, for example, cortisone, cortodoxone, flucetonide, fludrocortisone, difluorasone diacetate, flurandrenolone acetonide, medrysone, amcinafel, amcinafide, betamethasone and its esters, chloroprednisone, clocorelone, descinolone, desonide, dexamethasone, dichlorisone, difluprednate, flucloronide, flumethasone, flunisolide, fluocinonide, flucortolone, fluoromethalone, fluperolone, fluprednisolone, meprednisone, methylmeprednisolone, paramethasone, prednisolone and prednisone.

The subject compositions are also useful in antibacterial chemotherapy, e.g. in the treatment of skin conditions involving pathogenic bacteria. Typical antibacterial agents which may be used in this invention include sul fonamides, penicillins, cephalosporins, erythromycins, lincomycins, vancomycins, tetracyclines, chloramphenicols, streptomycins, etc. Typical examples of the foregoing include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxtcetracycline, minocycline, etc.

The subject compositions are also useful in protecting ultra-sensitive skin or even normally sensitive skin from damage or discomfort due to sunburn. Thus, actinic dermatitis may be avoided by application of a sunscreen, such as PABA or its well known derivatives or benzophenones in combination with one of the enhancers, to skin surfaces that are to be exposed to the sun; and the protective agent will be carried into the stratum corneum more successfully and will therefore be retained even when exposed to water or washing for a substantially longer period of time than when applied to the skin in conventional vehicles. This invention is particularly useful for ordinary suntan lotions used in activities involving swimming because the ultraviolet screening ingredients in the carriers are washed off the skin when it is immersed in water.

The subject compositions may also find use in treating scar tissue by applying agents which soften collagen, such as aminopropionitrile or penicillamine combined with one of the enhancers of this invention topically to the scar tissue.

Agents normally applied as eye drops, ear drops, or nose drops are more effective when combined with the enhancers of this invention.

Agents used in the diagnosis may be used more effectively when applied in combination with one of the enhancers of this invention. Patch tests to diagnose allergies may be effected promptly without scratching the skin or covering the area subjected to an allergen when the allergens are applied with one of the enhancers of this invention.

The subject compositions are also useful for topical application of cosmetic or esthetic agents. For example, compounds such as melanin-stimulating hormone (MSH) or dihydroxyacetone and the like are more effectively applied to the skin to simulate a suntan when they are used in combination with one of the enhancers of this invention. Depigmenting agents, such as hydroquinone, which bleach and lighten hyperpigmented skin are more effective when combined with one of the enhancers of this invention. Hair dyes also penetrate more completely and effectively when incorporated with enhancers of this invention. These enhancers are also useful in the compositions containing skin moisturizing agents.

The effectiveness of such topically applied materials as insect repellants or fragrances, such as perfumes and colognes, can be prolonged when such agents are applied in combination with the vehicles of this invention.

It is to be emphasized that the foregoing are simply examples of physiologically active agents including therapeutic and cosmetic agents having known effects for known conditions, which may be used more effectively for their known properties in accordance with this invention.

The term "physiologically active agent" is used herein to refer to a broad class of useful chemical and therapeutic agents including physiologically active steroids, antibiotics, anti-fungal agents, antibacterial agents, antineoplastic agents, allergens, antiinflammatory agents, antiemetics, antipruritic agents, antihistaminic agents, vasodilators, expectorants, analgesics, antiosteoporosis agents, sunscreen compounds, antiacne agents, collagen softening agents and other similar compounds. Cosmetic agents, hair and skin dyes, natural and synthetic hormones, perfumes, insect repellents, diagnostic agents and other such compounds may also be advantageously formulated with these penetration enhancers.

In addition, these membrane penetration enhancers may be used in transdermal applications in combination with ultrasound and iontophoresis.

Moreover, these penetration enhancers are useful in agriculture in the application of fertilizers, hormones, growth factors including micronutrients, insecticides, molluscicides, arachides, nematocides, rodenticides, herbicides, and other pesticides to plants, animals and pests. These penetration enhancers are also useful for penetration of micronutrients and chemical hybridization agents in seeds for enhanced plant growth. Of course, the appropriate dosage levels of all the physiologically active agents, without conjoint use of the penetration enhancing compounds of formula I, are known to those of ordinary skill in the art. These conventional dosage levels correspond to the upper range of dosage levels for compositions including a physiologically active agent and a compound of formula I as a penetration enhancer. However, because the delivery of the active agent is enhanced by compounds of the present invention, dosage levels significantly lower than conventional dosage levels may be used with success.

Systemically active agents are used in amounts calculated to achieve and maintain therapeutic blood levels in a human or other animal over the period of time desired. (The term "Animal" as used here encompasses humans as well as other animals, including particularly pets and other domestic animals.) These amounts vary with the potency of each systemically active substance, the amount required for the desired therapeutic or other effect, the rate of elimination or breakdown of the substance by the body once it has entered the bloodstream and the amount of penetration enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The present invention contemplates compositions of compounds of formula I, together with physiologically active agents from 0.05% to 100% of conventional dosage levels. The amount of compound of Formula I which may be used in the present invention is an effective, non-toxic amount for enhancing percutaneous absorption. Generally, for topical use the amount ranges between 0.1 to about 10 and preferably about 0.1 to 5 percent by weight of the composition. For transdermal enhancement of systemic agents, the amount of penetration enhancer which may be used in the invention varies from about 1 to 100 percent although adequate enhancement of penetration is generally found to occur in the range of about 1 to 30 percent by weight of the formulation to be delivered. For transdermal use, the penetration enhancers disclosed herein may be used in combination with the active agent or may be used separately as a pre-treatment of the skin or other body membranes through which the active agent is intended to be delivered.

Dosage forms for application to the skin or other membranes of humans and animals include creams, lotions, gels, ointments, suppositories, sprays, aerosols, buccal and sublingual tablets and any one of a variety of transdermal devices for use in the continuous administration of systemically active drugs by absorption through the skin, oral mucosa or other membranes, see for example, one or more of U.S. Pat. Nos. 3,598,122; 3,598,123; 3,731,683; 3,742, 951; 3,814,097; 3,921,636; 3,972,995; 3,993,072; 3,993, 073; 3,996,934; 4,031,894; 4,060,084; 4,069,307; 4,201, 211; 4,230,105; 4,292,299 and 4,292,303. U.S. Pat. No. 4,077,407 and the foregoing patents also disclose a variety of specific systemically active agents which may also be useful as in transdermal delivery, which disclosures are hereby incorporated herein by this reference.

The penetration enhancers of this invention may also be used in admixture with other penetration enhancers disclosed earlier and incorporated herein by reference.

Typical inert carriers which may be included in the foregoing dosage forms include conventional formulating materials, such as, for example, water, ethanol, 2-propanol, 1,2-propanediol, 1,3-butanediol, 2-octyldodecanol, 1,2,3,-propanetriol, oleyl alcohol, propanone, butanone, carboxylic acids such as lauric, oleic and linoleic acid, carboxylic acid esters such as isopropyl myristate, diisopropyl adipate and glyceryl oleate, acyclic and cyclic amides including N-methyl pyrrolidone, urea, freons, PEG-200, PEG-400, Polyvinyl pyrrolidone, fragrances, gel producing materials such as "Carbopol", stearyl alcohol, stearic acid, spermaceti, sorbitan monooleate, sorbital, "polysorbates", "Tweens", methyl cellulose etc., antimicrobial agent/preservative compositions including parabens, benzyl alcohol, potassium sorbate, sorbic acid, or a mixture thereof and antioxidant such as BHA or BHT. The dosage form may include a corticosteroid, such as hydrocortison, to prevent skin sensitization, a local anaesthetic, such as lidocaine or benzocaine to suppress local irritation.

The examples which follow illustrate the penetration enhancers and the compositions of the present invention. However, it is understood that the examples are intended only as illustrative and are not to be construed as in any way limiting to scope of this invention.

EXAMPLE 1

Preparation of 2-Ethanoylaminododecyl ethanoate

To a solution of 4.1 g of 2-aminododecanol, 5 g of triethylamine in 100 ml of dichloromethane was slowly added 3.2 ml of acetyl chloride. The reaction mixture was stirred for 3 hours and then quenched by pouring into ice. The aqueous solution was extracted with dichloromethane. The organic layer was washed with water, brine and then dried, filtered and concentrated to 5.7 g of a waxy solid. Recrystallization from ether/hexane gave 4.22 g (72.2%) of the desired amidoester as white crystals, m.p. 77°–79° C.

EXAMPLE 2

Preparation of 5-Amino-5-ethyl-2-carbobutoxyethyl-2-methyl-1,3-dioxane 7.46 g of 2-nitro-2-ethyl-1,3-propanediol, 8.61 g of butyl levulinate, 50 mg of p-toluenesulfonic acid in 50 ml of toluene was refluxed until no more water separated. The reaction mixture was cooled, washed with 2% sodium bicarbonate and water, dried and concentrated to give 13.65 g of 2-carbobutoxyethyl-2-methyl-5-nitro-5-ethyl-1,3-dioxane as a light yellow oil. This was dissolved in 50 ml of ethanol and hydrogenated over 1 g Raney Nickel catalyst at 60 under pressure. Distillation of the crude material at 160° C./3mm gave 11 g of the product.

EXAMPLE 3

Preparation of 5-Amino-5-ethyl-2-( 3 -heptyl )-1,3-dioxane

Procedure of Example 2 was repeated with 6.41 g of 2-ethylhexanal in place of butyl levulinate to give 11.6 g of the 5-nitro-1,3-dioxane, which was reduced and distilled at 135°–137° C./10 mm to give 9.23 g of the product.

EXAMPLE 4

Preparation of 5-Amino-5-hydroxymethyl-2-(3-heptyl)-1,3-dioxane

Procedure of Example 2 was repeated with 6.41 g of 2-ethylhexanal and 7.56 g of 2-(hydroxymethyl)-2-nitro-1,3-propanediol to give 11 g of 5-nitro-5-hydroxymethyl-1,3-dioxane derivative, which was reduced and distilled at 175°–178° C. to give 8.7 g of the product.

EXAMPLE 5

Preparation of 5-Amino-5-ethyl-2-undecyl-1,3-dioxane

Procedure of Example 2 was repeated with 9.216 g of dodecanal in place of butyl levulinate to give 13.4 g of the 5-nitro-1,3-dioxane derivative. Hydrogenation followed by distillation of the crude liquid at 150° C./1 mm gave 10.9 g of the product.

EXAMPLE 6

Preparation of erythro-5-Amino-2,2-dimethyl-4-[(E)-pentadec-1-enyl]-1,3-dioxane 17.6 g of nitroethanol was added to a solution of 22 g of (E)-hexa-dec-2-enal in 160 ml of triethylamine under an inert atmosphere. The mixture was stirred and the reaction was followed by t.l.c. After 4 days the reaction mixture was concentrated and the residue was dissolved in dichloromethane. This was washed with ice-cold 5% HCl, water, dried and concentrated to give an orange oil. This was flash chromatographed (silica gel: hexane/ethyl acetate, 7:3) to give 21.2 g of a mixture of threo- and erythro-nitro diols. 20.9 g of the isomeric mixture, 500 ml of 2,2-dimethoxypropane and 100 mg of camphor-10-sulfonic acid was refluxed overnight under an inert atmosphere. The reaction mixture was cooled, concentrated and the residue was dissolved in dichloromethane. The organic solution was washed with bicarbonate solution, water and brine. It was dried and concentrated to give a mixture of acetonides which were dissolved in benzene and the solution was refluxed for 8 hours in presence of Merck silica gel-60. The mixture was filtered and the silica gel was washed with warm benzene. The filtrate was concentrated and the residue was chromatographed to give 16.7 g of erythro-nitro acetonide. To a suspension of 5 g of lithium aluminum hydride in 200 ml of THF was added dropwise a solution of 16.7 g of the erythro-nitro acetonide in 100 ml of THF at room temperature. The reaction mixture was stirred for 8 hours and then excess LAH was quenched with water. THF was removed under reduced pressure, the residue was diluted with ethyl acetate and the mixture was filtered. The organic layer was separated, washed with water, brine and dried. Concentration of the filtrate under reduced pressure gave 15.1 g of erythro-5-Amino-4-[(E)-pentadec-1-enyl]-1,3-dioxane as an oil.

EXAMPLE 7

Preparation of erythro-5-Amino-2,2-dimethyl-4-pentadecyl-1,3-dioxane 3 g of the material obtained under Example 6 was dissolved in 50 ml of methanol and hydrogenated over 100 mg of platinum oxide catalyst. Filtration and concentration gave 2.86 g of an oil.

EXAMPLE 8

Preparation of erythro and threo-5-Amino-2,2-dimethyl-4-(2,6-dimethyl-5-heptenyl)-1,3-dioxane To a mixture of 11,565 g of racemic citronellal and 13.65 g of 2-nitroethanol was added 872 mg of KF and 1.21 g of tetra-n-butylammonium bromide in 75 ml of acetonitrile and the mixture was stirred at room temperature under an inert atmosphere. After 24 hours the reaction mixture was poured into ice-cold water and extracted with ether. The ether extract was washed with water and brine, dried and concentrated to give 15.6 g of isomeric mixture of 5,9-dimethyl-2-nitro-S-decene-1,3-diol.

A mixture of 14,715 g of the nitrodiol, 18.75 g of 2,2-dimethoxy-propane and 30 mg of p-toluenesulfonic acid in 150 ml of toluene was heated to reflux and water was removed by azeotropic distillation. The reaction mixture was cooled, diluted with ether and this was washed with water, brine, dried and concentrated in vacuo to give a yellow oil. The two isomers were separated by chromatography on Merck silica gel 60 and solution with benzene. 5.9 g of equatorial isomer was obtained first followed by 7.9 g of axial isomer, both as pale yellow oils.

To an ice-cold mixture of 4.5 g of the equatorial nitro isomer in 210 ml of ether and 13.5 ml of water was added freshly prepared amalgamated aluminum under stirring. The temperature of the reaction mixture was allowed to come to room temperature and then it was stirred for an additional 24 hours. The reaction mixture was filtered through celite and the filter cake was thoroughly washed with ether. The filtrate was concentrated to give an oil which was passed through neutral alumina to give 3 g of erythro isomer of 5-amino-2,2-dimethyl-4-(2,6-dimethyl-5-heptenyl)-1,3-dioxane as a colorless oil. 7.5 g of the axial nitro isomer was similarly reduced to give 4.99 g of the threo isomer as a colorless oil.

EXAMPLE 9

Preparation of 2-Octanoylaminododecyl octanoate

To a solution of 2 g of 2-aminododecanol, 3 g of triethylamine in 50 ml of dichloromethane is added 3.5 g of octanoyl chloride. The reaction mixture is stirred overnight and then quenched by pouring into ice. This is extracted with dichloromethane and the organic solution is washed with aqueous bicarbonate solution, water and brine. The organic phase is dried over magnesium sulfate, filtered and concentrated to give 3.8 g of the product.

EXAMPLE 10

Preparation of 2-Octadec-9-enoylamincdodecyl octadec-9-enoate

Example 9 is repeated under identical conditions with a solution of 2 g of 2-aminododecanol, 3 g of triethylamine in 50 ml of dichloromethane to which is added 6.3 g of oleoyl chloride. The reaction mixture is worked up as under Example 8 to give 5.1 g of product.

EXAMPLE 11

Preparation of 2-Ethanoylaminododecyl octadec-9-enoate

To a solution of 2.43 g of 2-ethanoylaminododecanol, 3 g of triethylamine in 50 ml of dichloromethane is added 3.2 g of oleoyl chloride. The reaction mixture is worked up as under Example 9 to give 4.2 g of product.

EXAMPLE 12

Preparation of 2,2-Dimethyl-5-dodecanoylamino-5-ethyl-1,3-dioxane 2,2-Dimethyl-5-amino-5-ethyl-1,3-dioxane is acylated wih dodecanoic acid in methylene chloride in the presence of DCC and 1-hydroxybenzo-triazole. Filtration and concentration gives the product.

EXAMPLE 13

Preparation of 5-Dodecanoylamino-5-methyl-1,3-dioxan-2-one

A solution of 2-methyl-2-nitro-1,3-propanediol and ethylene carbonate is heated overnight. The reaction mixture is diluted with ethyl acetate and the solution is washed with water. The organic phase is dried and concentrated to obtain 5-methyl-5-nitro-1,3-dioxan-2-one. This is dissolved in methanol and hydrogenated under pressure to give the 5amino compound which is acylated with dodecanoyl chloride to give the product.

EXAMPLE 14

Preparation of 5-Amino-5-undecyl-1,3-dioxan-2-one

2-Nitro-2-undecyl-1,3-propanediol is treated under identical conditions according to the reaction sequence outlined under Example 13 to give the product.

EXAMPLE 15

The following analgesic gel is prepared:

|  | % |
| --- | --- |
| Carbopol 941 | 1.5 |
| Diclofenac Na | 1 |
| 2-Propanal | 35 |
| Diisopropanolamine | 1.8 |
| Diisopropyl adipate | 5 |
| 5-Amino-5-ethyl-2-(3-heptyl)-1,3-dioxane | 2 |
| Water | 53.7 |

EXAMPLE 16

The following cream formulation is prepared:

|  | % |
| --- | --- |
| Isosorbide dinitrate | 1.0 |
| Glycerol monostearate | 5.5 |
| Polyoxyethylene stearate | 4.5 |
| C8–C18 fatty acid esters of a glycerol ethoxylated with about 7 moles of ethylene oxide | 8 |
| 5-Amino-5-ethyl-2-(3-heptyl)-1,3-dioxane | 2 |
| Sorbic acid | 0.165 |
| Ascorbyl palmitate | 0.055 |
| Citric acid | 0.1 |
| Na EDTA | 0.014 |
| Fragrance | 0.05 |
| Water | 78.616 |

This formulation is effective in the treatment of angina.

EXAMPLE 17

The following skin moisturizing formulation is prepared:

| | % |
|---|---|
| Pyrrolidonecarboxylic acid Na | 1 |
| Glycerine | 4 |
| Citric acid | 0.03 |
| Sodium citrate | 0.05 |
| Allantoin | 0.1 |
| Ethanol, 95% | 9 |
| Oleth-15 | 1 |
| Linaleic acid | 1 |
| 5-Amino-5-ethyl-2-(3-heptyl)-1,3-dioxane | 2 |
| Sunscreen agent | 0.1 |
| Water | 81.72 |

EXAMPLE 18

The following formulation for promoting hair growth is described.

| | % |
|---|---|
| Minoxidil | 2.0 |
| Benzyl nicotinate | 0.5 |
| Ethanol | 40.0 |
| 1,2-Propanediol | 20.0 |
| 5-Amino-5-ethyl-2-(3-heptyl)-1,3-dioxane | 5.0 |
| Ethyl aleate | 5.0 |
| Water | 27.5 |

EXAMPLE 19

The following solution formulation is prepared.

| | % |
|---|---|
| Griseofulvin | 1 |
| 5-Amino-5-ethyl-2-(3-heptyl)1,3-dioxane | 1.5 |
| C12–C15 benzoate | 5 |
| Fragrance | 0.1 |
| Ethanol | 92.4 |

This formulation is effective in the treatment of fungus infection.

EXAMPLE 20

The following depilatory gel is prepared.

| | % |
|---|---|
| Poloxamer 407 | 15.0 |
| Benzyl alcohol | 6.0 |
| Urea | 6.5 |
| alpha-Thioglycerol | 6.5 |
| 5-Amino-5-ethyl-2-(3-heptyl)-1,3-dioxane | 5.0 |
| Water | q.s. 100.0 |
| Sodium hydroxide | q.s. to pH 12.5 |

EXAMPLE 21

The following cream formulation is prepared:

| | % |
|---|---|
| Clindamycin Base | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| 5-Amino-5-ethyl-2-(3-heptyl)-1,3-dioxane | 1.9 |
| Sorbitol solution, U.S.P. | 5.5 |
| Sodium citrate | 0.5 |
| Chemoderm #844 | 0.2 |
| Purified water | 67.0 |

This formulation is effective in the treatment of ache.

EXAMPLE 22

The following solution formulations are prepared:

| | A (%) | B (%) |
|---|---|---|
| Clindamycin base | — | 1.0 |
| Clindamycin phosphate acid | 1.3 | — |
| Sodium hydroxide | 0.077 | — |
| 1M Hydrochloric acid | — | 2.27 |
| Disodium edentate.2H20 | 0.003 | 0.003 |
| Fragrances | 0.5 | 0.5 |
| 5-Amino-5-ethyl-2-(3-heptyl)-1,3-dioxane | 1.0 | 1.0 |
| Purified water | 20.0 | 17.73 |
| Isopropanal | 77.12 | 77.497 |

These solutions are effective for the treatment of ache in humans.

EXAMPLE 23

The following solution formulation is prepared:

| | % |
|---|---|
| Neomycin sulfate | 0.5 |
| Lidocaine | 0.5 |
| Hydrocortisone | 0.25 |
| 5-Amino-5-ethyl-2-(3-heptyl)-1,3-dioxane | 1.50 |
| Propylene glycol | 97.25 |

This solution is effective for the treatment of otitis in domestic animals.

EXAMPLE 24

The following sunscreen emulsion is prepared:

| | % |
|---|---|
| PABA | 2.0 |
| Benzyl alcohol | 0.5 |
| 5-Amino-5-ethyl-2-(3-heptyl)-1,3-dioxane | 2.0 |
| Polyethylene glycol | 9.0 |
| Isopropyl lanolate | 3.0 |
| Lantrol | 1.0 |
| Acetylated lanolin | 0.5 |
| C12–C15 benzoate | 5.0 |
| Diisopropyl adipate | 2.0 |
| Cetyl alcohol | 1.0 |
| Veegum | 1.0 |

-continued

|  | % |
| --- | --- |
| Propylene glycol | 3.0 |
| Purified water | 70.0 |

EXAMPLE 25

The following antineoplastic solution is prepared:

|  | % |
| --- | --- |
| 5-Fluorouracil | 5 |
| 5-Amino-5-ethyl-2-(3-heptyl)-1,3-dioxane | 1.5 |
| Polyethylene glycol | 5 |
| Purified water | 88.5 |

EXAMPLE 26

The following insect repellant atomizing spray is prepared:

|  | % |
| --- | --- |
| N,N-diethyltoluamide | 0.5 |
| 5-Amino-5-ethyl-2-(3-heptyl)-1,3-dioxane | 0.5 |
| Ethanol | 99 |

EXAMPLE 27

The following cream formulation may be prepared containing about 0,001 to 1 percent, with preferably 0.1% fluocinolone acetonide:

|  | % |
| --- | --- |
| Oil Phase |  |
| Fluocinolone acetonide | 0.1 |
| 5-Amino-5-ethyl-2-(3-heptyl)-1,3-dioxane | 1.6 |
| Cetyl alcohol | 9.3 |
| Stearyl alcohol | 1.3 |
| Glyceryl monostearate | 3.8 |
| Water Phase |  |
| Propylene glycol | 10 |
| Sodium dodecyl sulfate | 0.1 |
| Deionized water q.s. | 100 |

The steroid is dissolved in the vehicle and added to a stirred, cooling melt of the other ingredients. The preparation is particularly useful for the treatment of inflamed dermatoses by topical application to the affected skin area. The amount and frequency of application is in accordance with standard practice for topical application of this steroid. Penetration of this steroid in the inflamed tissue is enhanced and a therapeutic level is achieved more rapidly and sustained for longer duration than when the steroid is applied in the conventional formulation.

EXAMPLE 28

Transdermal patches containing nicotine with the following composition are prepared.

800 mg of Estane (B.F. Goodrich) is dissolved in 10 ml THF and 99 mg of nicotine, 50 mg of 1,2-propanediol and 50 mg of 5-Amino-5-ethyl-2-(3-heptyl)-1,3-dioxane is added. The homogenous solution is poured in a petri dish and the solvent is removed. The patches are die cut from the polymer film.

EXAMPLE 29

Transdermal patches containing progesterone with the following composition are prepared.

9.2 g of PDMS-382 (Dow Corning) pre-polymer, 300 mg of progesterone and 500 mg of 5-Amino-5-ethyl-2-(3-heptyl)-1,3-dioxane are mixed. One drop of polymerization initiator is added and the contents are thoroughly mixed. The mixture is degassed and allowed to polymerize in sheet molds for 24 hours at room temperature. After the curing is complete disks with 1 cm diameter are die cut.

EXAMPLE 30

Transdermal patches containing estradiol with the following compositions are prepared.

8.5 g of PDMS-382 (Dow Corning) pre-polymer, 1 g of estradiol, 500 mg of 5-Amino-5-ethyl-2-(3-heptyl)-1,3-dioxane are mixed and the patches are prepared as under Example 29.

EXAMPLE 31

EXAMPLES 15–30 are repeated, except the 5-Amino-5-ethyl-2 -(3-heptyl)-1,3-dioxane is replaced with an equimolar amount of each of the following listed compounds, and comparable results are obtained.

2-Ethanoylaminododecyl ethanoate
2-Ethanoylaminododecyl octadec-9-enoate
5-Amino-2,2-dimethyl-4-(pentadec-1-enyl)-1,3-dioxane
5-Amino-2,2-dimethyl-4-pentadecyl-1,3-dioxane
5-amino-4-dodecyl-1,3-dioxan-2-one
4-Dodecyl-5-ethanoylamino-1,3-dioxan-2-one
2-Ethanoylamino-3-octadecyloxypropyl ethanoate
5-Amino-2,2-dimethyl-4-(2,6-dimethyl-5-heptenyl)1,3-dioxane
5-Amino-5-ethyl-2-undecyl-1,3-dioxane
2,2-Dimethyl-5-dodecanoylamino-5-ethyl-1,3-dioxane
5-Amino-5-hydroxymethyl-2-(3-heptyl)-1,3-dioxane
5-Amino-5-ethyl-2-carbobutoxyethyl-2-methyl-1,3-dioxane

EXAMPLE 32

The compounds of the present invention are tested in vitro as penetration enhancers according to the procedure outlined below.

Human stratum corneum is isolated from full thickness human skin as described by Bronaugh et al., J. Pharm. Sci. 75, 1094 (1986). The skin is placed between the donor and the receptor compartments of diffusion cells in such a way that the dermal side of the skin faces the receptor compartment which is filled with normal saline (pH 7.2–7.4). The stratum comeum is equilibrated at 37° C. overnight prior to the application of a topical formulation or transdermal patch. All formulations are studied in triplicate.

About 500 mg of the following three Isosorbide Dinitrate (ISDN) formulations (40% ISDN & 60% Lactose) are applied to cover the stratum corneum surface within the donor compartment. The entire contents of the receptor compartment are removed at specific time intervals over 51 hours and replenished with fresh saline. The aliquots are analyzed by HPLC and the average cumulative amount of ISDN in micrograms permeating over the study period is calculated.

The results show that the formulations containing the penetration enhancers of the present invention show superior permeation as compared to control.

While particular embodiments of the invention have been described it will be understood of course that the invention is not limited thereto since many obvious modifications can be made and it is intended to include within this invention any such modifications as will fall within the scope of appended claims.

What is claimed is:

1. A composition for enhancing absorption of a topically administered formulation through dermal or mucosal tissue, for local or systemic application, comprising an admixture of an effective amount of a physiologically active agent and a non-toxic, effective amount of a membrane penetration enhancing agent of formula I,

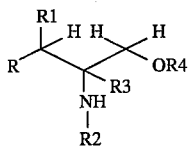

wherein

R is selected from H, and an aliphatic hydrocarbon group with from about 1 to about 20 carbon atoms, optionally containing a heteroatom in the hydrocarbon chain;

R1 is selected from H, OH or O-CO-RS, where R5 is an aliphatic hydrocarbon group with from about 1 to about 18 carbon atoms;

R2 is selected from H, a lower aliphatic hydrocarbon group, acyl, hydroxyacyl or alkoyloxyacyl group with from up to about 40 carbon atoms;

R3 is selected from H, an aliphatic hydrocarbon group with up to about 16 carbon atoms, unsubstituted or substituted with hydroxy, acyloxy or alkylthio, or an aryl or aralkyl group; and R4 is H or an acyl group with from about 2 to about 18 carbon atoms; or R, R2 and R3 are as defined above, and R1 and R4 together form compounds having a 1,3-dioxane ring, of the structure

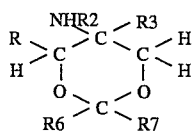

wherein, R6 and R7 are selected from H, an aliphatic hydrocarbon group unsubstituted or substituted with hydroxy, acyloxy, or carboalkoxy, or an aryl group, or they may combine to form a carbonyl group, or a physiologically acceptable salt thereof.

2. The composition of claim 1 wherein in said formula I R is an alkyl or alkenyl group with from about 1 to about 20 carbon atoms, $R^1$ and $R^3$ are hydrogen, $R^2$ is an acyl group with from about 1 to about 30 carbon atoms, and $R^4$ is an acyl group with from about 2 to about 18 carbon atoms, and the other substituents are as defined in claim 1.

3. The composition of claim 1 wherein in said formula I $R^1$ is -O-CO-$R^5$, wherein $R^5$ is an aliphatic hydrocarbon group from about 1 to about 18 carbon atoms, and the other substituents are as defined in claim 1.

4. The composition of claim 1 wherein in said formula I $R^2$ is H or acyl, $R^3$ is hydrogen, $R^1$ and $R^4$ together form a 1,3-dioxane ring, and the other substituents are as defined in claim 1.

5. The composition of claim 1 wherein in said formula I $R^2$ is hydrogen acyl, $R^3$ is alkyl, aryl, aralkyl, hydroxyalkyl, acyloxyalkyl or alkylthioalkyl, R and $R^4$ are hydrogen, $R^1$ and $R^4$ together form a 1,3-dioxane ring, and the other substituents are as defined in claim 1.

6. The composition of claim 1 wherein said membrane penetration enhancing agent is selected from the group consisting of 2-Ethanoylaminododecyl ethanoate, 2-Octanoylaminododecyl octanoate, 2-Octadec-9-enoylaminododecyl octadec-9-enoate, 2-Octadec-9-enoylaminododecyl ethanoate, 2-Octadecanoylaminooctadec-4-enyl 1,3-diethanoate, 2-Ethanoylaminooctadec-4-enyl 1,3-diethanoate, 2-Ethanoylaminooctadecyl 1,3-diethanoate, 5-Amino-2,2-dimethyl-4-(pentadec-1-enyl)-1,3-dioxane, 5-Amino-2,2-dimethyl-4-pentadecyl-1,3-dioxane, 5-Amino-4-(pentadec-1-enyl)-1,3-dioxan-2-one, 5-amino-4-dodecyl-1,3-dioxan-2-one, 4-Dodecyl-5-ethanoylamino-1,3-dioxan-2-one, 2-Ethanoylaminododecyl octadec-9-enoate, 2-Ethanoylamino-3-octadecyloxypropyl ethanoate, 5-Amino-2,2-dimethyl-4-(2,6,10,14-tetramethylpentadecyl)1,3-dioxane, 5-Amino-2,2-dimethyl-4-(2,6-dimethyl-5-heptenyl)-1,3-dioxane, 5-amino-5-ethyl-2-undecyl-1,3-dioxane, 5-amino-2,2-dimethyl-5-undecyl-1,3-dioxane, 2,2-Dimethyl-5-dodecanoylamino-5-ethyl-1,3-dioxane, 5-Amino-5-ethyl-2-(3-heptyl)-1,3-dioxane, 5-Amino-5-hydroxymethyl-2-(3-heptyl)-1,3-dioxane, 5-Amino-5-ethyl-2-carbobutoxyethyl-2-methyl-1,3-dioxane, 5-Dodecanoylamino-5-methyl-1,3-dioxan-2-one, and 5-Amino-5-undecyl-1,3-dioxan-2-one, and a physiologically acceptable salt thereof.

7. The composition of claim 1 wherein said physiologically active agent is selected from the group consisting of analgesics, antiinflammatory agents, tranquilizers, cardiovascular agents, antiosteoporosis agents, antifertility agents, antiasthmatic agents, antineoplastic and antiviral agents, antibiotics, antifungal agents, antpsoriatic agents and narcotic antagonists.

8. The composition of claim 7 wherein said physiologically active agent is an analgesic selected from the group consisting of hydromorphone, fentanyl and bupronorphine; an antiinflammatory agent selected from the group consisting of indomethacin, diclofenac and ketoprofen; a tranquilizer selected from the group consisting of triazolam, alprazolam and diazepam; a cardiovascular agent selected from the group consisting of isosorbide dinitrate, clonidine, propranolol, nifedipine, nicardipine, diltiazem, lisinopril; an antiosteoporosis agent selected from the group consisting of estradiol, ethinyl estradiol and 1,25-dihydroxy-7-dehydrocholesterol; an antifertility agent selected from the group consisting of progesterone and medroxyprogesterone; an antiasthmatic agent selected from the group consisting of theophylline, albuterol and metaproterenol; an antineoplastic and antiviral agent selected from the group consisting of acyclovir, vidarabine, ribavirin, cytarabine, AZT and 5-fluorouracil; an antibiotic selected from the group consisting of cefoxitin, clindamycin, gentamycin, erythromycin and fusidic acid; an antifungal agent selected from the group consisting of miconazole, econazole, tolnaftate and griseofulvin; an antipsoriatic agent selected from the group consisting of novobiocin, naldixic acid and its prodrugs and methotrexate and a narcotic antagonist selected from the group consisting of naloxone and naltrexone.

9. The composition of claim 1 further comprising pharmaceutically acceptable excipients.

10. A method of enhancing the rate of dermal or mucosal membrane absorption of a topically administrable composition for local or systemic application, said method comprising the step of applying to a mucosal or dermal tissue of a patient a therapeutically effective dosage amount of a physiologically active agent in admixture with a non-toxic, effective amount of a membrane penetration enhancing agent having the structure shown in formula I,

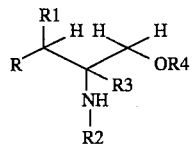

wherein

R is selected from H, and an aliphatic hydrocarbon group with from about 1 to about 20 carbon atoms, optionally containing a heteroatom in the hydrocarbon chain;

R1 is selected from H, OH or O-CO-R5, where R5 is an aliphatic hydrocarbon group with from about 1 to about 18 carbon atoms;

R2 is selected from H, a lower aliphatic hydrocarbon group, acyl, hydroxyacyl or alkoxyoxyacyl group with up to about 40 carbon atoms;

R3 is selected from H, an aliphatic hydrocarbon group with up to about 16 carbon atoms unsubstituted or substituted with hydroxy, acyloxy or alkylthio, or an aryl or aralkyl group; and R4 is H or an acyl group with from 2 to about 18 carbon atoms; or R, R2 and R3 are as defined above, and R1 and R4 together form a compound having a 1,3-dioxane ring, of the structure

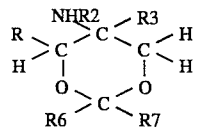

wherein, R6 and R7 are selected from H, an aliphatic hydrocarbon group unsubstituted or substituted with hydroxy, acyloxy, or carbalkoxy, or an aryl group, or they may combine to form a carbonyl group.

11. The method of claim 10 wherein in said formula I R is an alkyl group with from about 1 to about 20 carbon atoms, $R^1$ and $R^3$ are hydrogen, $R^2$ is an acyl group with from about 1 to about 30 carbon atoms, and $R^4$ is an acyl group with from about 1 to about 18 carbon atoms, and the other substituents are as defined in claim 10.

12. The method of claim 10 wherein in said formula I $R^1$ is O-CO-$R^5$, wherein $R^5$ is an aliphatic hydrocarbon group from about 1 to about 18 carbon atoms, and the other substituents are as defined in claim 10.

13. The method of claim 10 wherein in said formula I $R^2$ is H or acyl $R^3$ is hydrogen, $R^1$ and $R^4$ together form a 1,3-dioxane ring, and the other substituents are as defined in claim 10.

14. The method of claim 10 wherein in said formula I $R^2$ is hydrogen or acyl, $R^3$ is alkyl, aryl, aralkyl, hydroxyalkyl, acyloxyalkyl or alkylthioalkyl, R and $R^4$ are hydrogen, $R^1$ and $R^4$ together form a 1,3-dioxane ring, and the other substituents are as defined in claim 10.

15. The method of claim 10 wherein said membrane penetration enhancing agent is selected from the group consisting of 2-Ethanoylaminododecyl ethanoate, 2-Octanoylaminododecyl octanoate, 2-Octadec-9-enoylaminododecyl octadec-9-enoate, 2-Octadec-9-enoylaminododecyl ethanoate, 2-Octadecanoylaminooctadec-4-enyl 1,3-diethanoate, 2-Ethanoylaminooctadec-4-enyl 1,3-diethanoate, 2-Ethanoylaminooctadecyl 1,3-diethanoate, 5-Amino-2,2-dimethyl-4-(pentadec-1-enyl)-1,3-dioxane, 5-Amino-2,2-dimethyl-4-pentadecyl-1,3-dioxane, 5-Amino-4-(pentadec-1-enyl)-1,3-dioxan-2-one, 5-amino-4-dodecyl-1,3-dioxan-2-one, 4-Dodecyl-5-ethanoylamino-1,3-dioxan-2-one, 2-Ethanoylaminododecyl octadec-9-enoate, 2-Ethanoylamino-3-octadecyloxypropyl ethanoate, 5-Amino-2,2-dimethyl-4-(2,6,10,14-tetramethylpentadecyl)-1,3-dioxane, 5-Amino-2,2-dimethyl-4-(2,6-dimethyl-5-heptenyl)-1,3dioxane, 5-amino-5-ethyl-2-undecyl-1,3-dioxane, 5-amino-2,2-dimethyl-5-undecyl-1,3-dioxane, 2,2-Dimethyl-5-dodecanoylamino-5-ethyl-1,3-dioxane, 5-Amino-5-ethyl-2-(3-heptyl)-1,3-dioxane, 5-Amino-5-hydroxymethyl-2-(3-heptyl)-1,3 -dioxane, 5-Amino-5-ethyl-2-carbobutoxyethyl-2-methyl-1,3-dioxane, 5-Dodecanoylamino-5-methyl-1,3-dioxan-2-one, and 5-Amino-5-undecyl-1,3-dioxan-2-one, a physiologically acceptable salt thereof.

16. The method of claim 10 wherein said physiologically active agent is selected from The group consisting of analgesics, antiinflammatory agents, tranquilizers, cardiovascular agents, antiosteoporosis agents, antifertility agents, antiasthmatic agents, antineoplastic and antiviral agents, antibiotics, antifungal agents, antipsoriatic agents and narcotic antagonists.

17. The method of claim 10 wherein said physiologically active agent is an analgesic selected from the group consisting of hydromorphone, fentanyl and bupronorphine; an antiinflammatory agent selected from the group consisting of indomethacin, diclofenac and ketoprofen; a tranquilizer selected from the group consisting of triazolam, alprazolam and diazepam; a cardiovascular agent selected from the group consisting of isosorbide dinitrate, clonidine, propranolol, nifedipine, nicardipine, diltiazem, lisinopril; an antiosteoporosis agent selected from the group consisting of estradiol, ethinyl estradiol and 1,25-dihydroxy-7-dehydrocholesterol; an antifertility agent selected from the group consisting of progesterone and medroxyprogesterone; an antiasthmatic agent selected from the group consisting of theophylline, albuterol and metaproterenol; an antineoplastic and antiviral agent selected from the group consisting of acyclovir, vidarabine, ribavirin, cytarabine, AZT and 5-fluorouracil; an antibiotic selected from the group consisting of cefoxitin, clindamycin, gentamycin, erythromycin and fusidic acid; an antifungal agent selected from the group consisting of miconazole, econazole, tolnaftate and griseofulvin; an antipsoriatic agent selected from the group consisting of novobiocin, naldixic acid and its prodrugs and methotrexate and a narcotic antagonist selected from the group consisting of naloxone and naltrexone.

18. A method of treating a physiological dissorder in a human or other animal in need thereof comprising applying to the skin or mucosal membrane of the human or other animal a composition comprising a physiological active agent and a non-toxic amount sufficient to assure penetration through the skin or mucous membrane of an agent of Formula I:

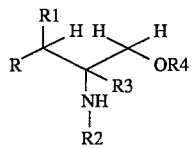

wherein:
R is selected from H, and an aliphatic hydrocarbon group with from about 1 to about 20 carbon atoms, optionally containing a heteroatom in the hydrocarbon chain;

$R_1$ is selected from H, OH or O-CO-RS, where $R_5$ is an aliphatic hydrocarbon group with from about 1 to about 18 carbon atoms;

$R_2$ is selected from H, a lower aliphatic hydrocarbon group, acyl, hydroxyacyl or alkoyloxyacyl group with up to about 40 carbon atoms;

$R_3$ is selected from H, an aliphatic hydrocarbon group with up to about 16 carbon atoms, unsubstituted or substituted with hydroxy, acyloxy or alkylthio or an aryl or aralkyl group; and $R_4$ is H or an acyl group with from about 1 to about 18 carbon atoms; or $R_1$ OH and $R_4$ are combined to form a 1,3-dioxane ring,

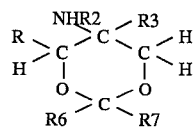

wherein, $R_6$ and $R_7$ are selected from H, an aliphatic hydrocarbon group unsubstituted or substituted with hydroxy, acyloxy, or carboalkoxy, or an aryl group, or they may combine to form a carbonyl group, or a physiologically acceptable salt thereof.

19. The method of claim 18 wherein physiologically active agent is a antibacterial agent.

20. The method of claim 19 wherein the antibacterial agent is an antibiotic.

21. The method of claim 20 wherein the antibiotic is selected from the group consisting of lincomycin, clindamycin, erythromycin and pharmaceutically acceptable salts thereof.

22. The method of claim 18 wherein the physiologically active material is selected from the group consisting of a physiologically active steroid, antifungal agent and antipsoriatic agent.

23. The method of claim 18 wherein the physiologically active agent is acyclovir.

24. The method of claim 18 wherein the physiologically active agent is diclofenac.

25. The method of claim 18 wherein the physiologically active agent is pyrrolidone carboxylic acid or a pharmaceutically acceptable salt thereof.

26. The method of claim 18 wherein the composition comprises an effective amount of physiologically active agent and an effective penetrating amount of 5-Amino-5-ethyl-2-(3-heptyl)-1,3-dioxane.

* * * * *

UNITED STATES PATENT AND TRADEMARK OFFICE
CERTIFICATE OF CORRECTION

PATENT NO. : 5,482,965
DATED : January 9, 1996
INVENTOR(S) : Vithal J. Rajadhyaksha It is certified that error appears in the above-indentified patent and that said Letters Patent is hereby corrected as shown below:

Column 19, line 37, change "O-CO-RS" to --O-CO-R5--

Column 21, line 65, change "carbonyl group." to --carbonyl group, or a physiologically acceptable salt thereof--

Column 22, line 9, change "$R^2$ is H or acyl" to --$R^2$ is hydrogen or acyl--

Column 22, line 10, change "$R^3$ is hydrogen, $R^1$ and $R^4$ together" to --$R^3$ is alkyl, aryl, aralkyl, hydroxyalkyl, acylaxyalakyl, or alkylthioalkyl, R and $R^4$ are hydrogen, $R^1$ and $R^4$ together--

Column 22, line 54, change "from The group" to --from the group--

Column 23, line 18, change "treating a physiological disorder in a human" to --treating a human or--

Column 23, line 19, change "animal in need thereof comprising" to --animal comprising--

Column 23, line 21, change "a physiological active agent and a non-toxic" to --a non-toxic--

Column 23, line 37, change "O-CO-RS" to --O-CO-R5--

Signed and Sealed this

Seventeenth Day of September, 1996

Attest:

BRUCE LEHMAN

Attesting Officer

Commissioner of Patents and Trademarks